United States Patent
Davies

(10) Patent No.: US 6,654,696 B1
(45) Date of Patent: Nov. 25, 2003

(54) METHOD FOR NUCLEIC ACID SEQUENCE DETERMINATION USING CODES FOR ERROR CORRECTION

(76) Inventor: Stephen W. Davies, 385 Ocean Blvd., Apt 4F, Long Branch, NJ (US) 07740

( * ) Notice: Subject to any disclaimer, the term of this patent is extended or adjusted under 35 U.S.C. 154(b) by 0 days.

(21) Appl. No.: 09/472,795

(22) Filed: Dec. 28, 1999

(30) Foreign Application Priority Data

Dec. 29, 1998 (CA) .............................................. 2256128

(51) Int. Cl.[7] .......................... G06F 19/00; G01N 33/48; C12Q 1/68; C12P 19/34
(52) U.S. Cl. ............................ 702/20; 435/6; 435/91.2; 702/19; 702/21
(58) Field of Search ............................. 702/19, 20, 21; 435/6, 91.2

(56) References Cited

U.S. PATENT DOCUMENTS 5,308,751 A  *  5/1994  Ohkawa et al. ................. 435/6
6,404,907 B1 *  6/2002  Gilchrist et al. ............ 382/129

* cited by examiner

*Primary Examiner*—Ardin H. Marschel

(57) ABSTRACT

The recovery of the sequence of bases in a dideoxyribonucleic acid (DNA) molecule is important for both research and medical applications. The standard processing techniques are prone to error. This invention creates from the template a new set of molecules which introduce an error correcting code as might be used in data communications. After the usual processing associated with DNA sequencing, the code can be used to reduce the errors in the estimated sequence.

19 Claims, No Drawings

METHOD FOR NUCLEIC ACID SEQUENCE DETERMINATION USING CODES FOR ERROR CORRECTION

CROSS-REFERENCE TO RELATED APPLICATIONS

This patent application claims the foreign priority of Canadian Patent Application Number 2,256,128, Dec. 29, 1998.

STATEMENT REGARDING FEDERALLY SPONSORED RESEARCH OR DEVELOPMENT

United States Federal sponsorship was not involved in this work.

REFERENCE TO A MICROFICHE APPENDIX

Not applicable.

BACKGROUND OF THE INVENTION

References

1. Brown, T. A., "DNA Sequencing: The Basics", Oxford University Press, New York, 1994.
2. Tibbetts, C., Bowling, J., "Method and Apparatus for Automatic Nucleic Acid Sequence Determination", U.S. Pat. No. 5,365,455, Nov. 15, 1994.
3. Lee, E., Messerschchmitt, D., "Digital Communication", (2nd Ed.), Kluwer, New York, 1994.
4. Proakis, J. G., "Digital Communications", (3rd Ed.), McGraw-Hill Inc., New York, 1995.
5. Blahut, R. E., "Theory and Practice of Error Control Codes", Addison-Wesley Publishing Co., Reading, Mass., 1983.

DeoxyriboNucleic Acid (DNA) encodes genetic information by specific base type at each point in a sequence of bases. For research and medical purposes it is desirable to recover the sequence, $\underline{x}=\{x_i, i=1, \ldots, N\}$, where $x_i$ is one of the four bases {adenine(A), cytosine(C), guanine(G), thymine(T)} that encode the genetic information; for some medical tests, it is not necessary to recover the whole sequence but rather identify the base type at certain key locations in the sequence.

In Sanger sequencing [1], the DNA template to be sequenced is chemically processed to encode sequence position by molecular weight and base type by the presence or absence of a fluorescent or radioactive marker. Gel electrophoresis is used to separate the molecules by length, translating molecular size into time of passage past a detector in the case of automated DNA sequencing [2]. Four time-series $y_{n,k}$, where n={A,C,G,T} and k is the time sample index, are recorded, each of which corresponds to one of the four possible chemical base types. At a given time, a high-level signal (peak) should appear in only one of the series; this indicates the base type at that point in the sequence. We shall refer to the recorded time series as the 'DNA time-series' for the remainder of this document.

The fragment of DNA to be sequenced and the starting position for sequencing are identified through the use of primers [1]. Primers are short strands of DNA that are complementary to the target DNA sequence at the point of interest. Primers bind to the DNA template at that point and permit copying of the DNA using a DNA polymerase. This copying process is used in fragment selection and in sequencing as part of the process that encodes sequence position by molecular weight. In the later case, the recovered sequence position would be relative to the primer's location with respect to the original DNA template.

In practice, the recovery of the sequence is complicated by undesirable signal features. Errors in DNA sequencing can have dangerous implications for the pharmaceutical and medical communities. To reduce errors, the entire sequencing process is repeated until a consensus sequence may be reached. This process is costly. Thus, there exists a need for a method to reduce error rate so that the costs and risks of DNA sequencing and testing may be minimized.

In data communications [3],[4] time-series similar to the DNA time-series described above are used to represent sequential information such as the text of a document. A receiving device will examine the time-series to recover an estimate of the original text. However, noise and distortion imposed on the time-series during its passage through a transmission medium such as a radio link or telephone wires can lead to errors in the recovery of the original information. To reduce the chance of error, the original data may first be passed through a coder that imposes a mathematical code on the data [3][5]. This introduces redundant information that a decoder added to the receiver uses to identify and correct errors. A large variety of codes have been created [5].

BRIEF SUMMARY OF THE INVENTION

With a goal of reducing errors, this invention imposes a code by creating a new family of molecules from the DNA fragment of interest. This new family of molecules consists of fragments offset from the start of the original fragment by using different primers to achieve different offsets.

Standard codes may then be implemented by combining different proportions of the different fragments. This mixture is then used in the usual testing or sequencing process, such as gel electrophoresis, to recover the coded DNA time-series. The sequencer or tester then decodes the time-series by hypothesizing what the time series should have been for each possible sequence and choosing the sequence that yields the best match to the observed time-series.

BRIEF DESCRIPTION OF THE SEVERAL VIEWS OF THE DRAWING

Not applicable.

DETAILED DESCRIPTION OF THE INVENTION

The overall processing is best illustrated by a simple example. The extensions to the general case will be discussed after the example.

Consider an original DNA template

SEQ ID NO:1 CAAGTACCGAGCTGA where the letters A, C, G and T correspond to the four possible base types. Consider sequencing starting with the ninth base in the sequence. An appropriate primer for the sequencing reactions would then be complementary to

GTACC and given this primer the sequencing process may be carried out as is common to the art. The sequence thus obtained if no errors occurred would be

GAGCTGA.

To add coding in this example, two additional primers are included which are complementary to the fragments

CAAGT

AGTAC respectively. These primers, if used separately, would then lead to obtaining the following sequences

SEQ ID NO:2 ACCGAGCTGA

CGAGCTGA respectively, if the common sequencing process was carried out. These correspond to priming for sequences starting at the sixth and eighth positions in the original sequence. For our coding example, however, all three primers are used, either in the same reaction vessel or separately with the products then combined in to the same reaction vessel. Now on sequencing the combination, rather than seeing a single peak at each base position corresponding to a single base type, it is possible for several base types to be indicated simultaneously. The three primers lead to the superposition of the three sequences

SEQ ID NO:2 ACCGAGCTGA

CGAGCTGA

GAGCTGA.

For example, in the second base position, peaks should appear in the time-series corresponding to the bases C, G and A while no peak should appear in the second base position for the T time-series. At locations where two of these sequences have a common base type, the corresponding peak height should be double that of the case where only one sequence had a base of that type at that position. At locations where three of these sequences have a common base type, the corresponding peak height should be thrice that of the case where only one sequence had a base of that type at that position. This leads to an idealized representation of the peak heights of the four channels of the DNA time-series as a function of sequence position as

| A | 1 | 1 | 1 | 0 | 1 | 0 | 1 | 1 | 0 | 1 |
|---|---|---|---|---|---|---|---|---|---|---|
| C | 1 | 1 | 1 | 1 | 1 | 0 | 1 | 0 | 0 | 0 |
| G | 1 | 1 | 1 | 2 | 0 | 2 | 1 | 0 | 1 | 0 |
| T | 0 | 0 | 0 | 0 | 1 | 1 | 0 | 1 | 0 | 0. |

To illustrate the error correcting ability of this code, consider an error occurring in the reactions (or electrophoresis and detection) associated with the primer GTACC such that the corresponding sequence was GAACTGA rather than GAGCTGA. Then, assuming the other reactions were error free, the three primers lead to the superposition of the three sequences

SEQ ID NO:2 ACCGAGCTGA

CGAGCTGA

GAACTGA and the peak heights of the four channels of the DNA time-series as a function of sequence position are

| A | 1 | 1 | 2 | 0 | 1 | 0 | 1 | 1 | 0 | 1 |
|---|---|---|---|---|---|---|---|---|---|---|
| C | 1 | 1 | 1 | 1 | 0 | 1 | 0 | 0 | 0 | |
| G | 1 | 1 | 0 | 2 | 0 | 2 | 1 | 0 | 1 | 0 |
| T | 0 | 0 | 0 | 0 | 1 | 1 | 0 | 1 | 0 | 0 |

This differs from the original table of peak heights only in at the third base position. However, the hypothesized peak table corresponding to our error having in fact been the right sequence (i.e. the original template being SEQ ID NO:1 CAAGTACCGAACTGA) is

| A | 1 | 1 | 2 | 1 | 1 | 1 | 1 | 1 | 0 | 1 |
|---|---|---|---|---|---|---|---|---|---|---|
| C | 1 | 1 | 1 | 1 | 1 | 0 | 1 | 0 | 0 | 0 |
| G | 1 | 1 | 0 | 1 | 0 | 1 | 1 | 0 | 1 | 0 |
| T | 0 | 0 | 0 | 0 | 1 | 1 | 0 | 1 | 0 | 0 |

This differs from the observation at the fourth and sixth base positions. In the language of coding theory, these two differences correspond to a Hamming distance of two where as the correct hypothesis differs only at the third base and thus has a Hamming distance of one. The rule to be used in the simple decoder is to choose the hypothesis with the least Hamming distance. Thus, for this case of a single error associated with one primer, the decoder would in fact choose the correct sequence, GAGCTGA, where as the standard processing using only a single primer (GTACC) would have erroneously estimated the sequence to be GAACTGA.

Note that this example assumed exact estimates of the peak heights were available. As is well known in the art of communications, this presumption corresponds to "hard decoding". If the actual time-series had been compared with hypothesized idealized time-series then the decoding process would in communications be referred to as "soft decoding".

Extending this example to the general case yields the preferred description of the invention as described in the following three steps.

Step 1—Conduct sequencing reactions using multiple primers pointing to different points in the sequence. By changing the relative proportions of the primers, it is possible to compensate for different reactivities of the primer, polymerase and template complex. Also, fractional weights, as might be utilized in sophisticated coding schemes, may be obtained. Select a code from the literature with the desired error correcting characteristics. Note that a wide variety of such codes are available and that this invention does not refer to a specific code but rather the process by which codes common to the art of communications may be used in DNA sequencing. The general class of convolutional codes are directly applicable as they correspond to weighted sums of sequences with different offsets into the original information sequence.

Step 2—Through the usual art of DNA sequencing obtain time-series corresponding to the four base types. Use these series directly if soft decoding is to be employed. If hard decoding is to be employed, process the time-series to recover peak heights at each base position.

Step 3—Compare the time-series (or peak heights in the case of hard decoding) to the ideal time-series (or peak heights in the case of hard coding) for different hypothesized sequences. The model used in generation of these time-series may account for effects inherent in the electrophoresis process such as varying peak shape with sequence position. Choose as the estimated sequence the hypothesized sequence that yields the time-series (or peak heights) closest in Euclidian distance (or Hamming distance in the case of hard coding).

What is claimed is:

1. A method for determining a target sequence of a single-stranded DNA molecule comprising the steps of:
   (a) forming, through a plurality of chemical reactions, a set of products from said single-stranded DNA molecule wherein:
      (i) said set of products represent subsequences of the single-stranded DNA molecule;
      (ii) members of said set of products are selected according to a code; and
      (iii) said code specifies a set of weights with which to set the proportions of each of different members of said set of products;
   (b) obtaining a combined set of signals from said set of products; and
   (c) applying means using said code and said set of signals to recover a sequence of bases;
wherein the target sequence of nucleic acid is determined with accuracy.

2. The invention defined in claim 1 wherein said means using said code and said set of signals to recover said sequence of bases is hard decoding implemented by:
   (a) forming from said set of signals a set of quantized signals with the value of each sample of each of said quantized signals being directly translatable to the number of offsets contributing significantly to the peak at that location;
   (b) forming a measure of distance between said quantized signals and each set of a plurality of sets of test signals where each set of test signals is formed based on a different hypothesized sequence; and
   (c) choosing as the determined target sequence the hypothesized sequence whose set of test signals had the shortest distance to said quantized signals;
whereby an accurate sequence is obtained.

3. The invention defined in claim 1 wherein said means using said code and said set of signals to recover said sequence of bases is soft decoding implemented by:
   (a) forming a measure of distance between the said signals and each set of a plurality of sets of test signals where each set of test signals is formed based on a different hypothesized sequence; and
   (b) choosing as the determined target sequence the hypothesized sequence whose test signals had the shortest distance to said signals;
whereby an accurate sequence is obtained.

4. The invention as defined in claim 1 wherein said set of products are formed from fragments whose starting sequences are offset from the start sequence of said single-stranded DNA molecule via using primers to achieve different offsets.

5. The invention defined in claim 4 wherein said means using said code and said set of signals to recover said sequence of bases is hard decoding implemented by:
   (a) forming from said set of signals a set of quantized signals with the value of each sample of each of said quantized signals being directly translatable to the number of offsets contributing significantly to the peak at that location;
   (b) forming a measure of distance between said quantized signals and each set of a plurality of sets of test signals where each set of test signals is formed based on a different hypothesized sequence; and
   (c) choosing as the determined target sequence the hypothesized sequence whose set of test signals had the shortest distance to said quantized signals;
whereby an accurate sequence is obtained.

6. The invention defined in claim 4 wherein said means using said code and said set of signals to recover said sequence of bases is soft decoding implemented by:
   (a) forming a measure of distance between the said signals and each set of a plurality of sets of test signals where each set of test signals is formed based on a different hypothesized sequence; and
   (b) choosing as the determined target sequence the hypothesized sequence whose test signals had the shortest distance to said signals;
whereby an accurate sequence is obtained.

7. The invention as defined in claim 1 wherein at least one of said set of weights has a value substantially different than that of the other members of said set of weights.

8. The invention defined in claim 7 wherein said means using said code and said set of signals to recover said sequence of bases is hard decoding implemented by:
   (a) forming from said set of signals a set of quantized signals with the value of each sample of each of said quantized signals being directly translatable to the number of offsets contributing significantly to the peak at that location;
   (b) forming a measure of distance between said quantized signals and each set of a plurality of sets of test signals where each set of test signals is formed based on a different hypothesized sequence; and (c) choosing as the determined target sequence the hypothesized sequence whose set of test signals had the shortest distance to said quantized signals;

whereby an accurate sequence is obtained.

9. The invention defined in claim 7 wherein said means using said code and said set of signals to recover said sequence of bases is soft decoding implemented by:

(a) forming a measure of distance between the said signals and each set of a plurality of sets of test signals where each set of test signals is formed based on a different hypothesized sequence; and (b) choosing as the determined target sequence the hypothesized sequence whose test signals had the shortest distance to said signals;

whereby an accurate sequence is obtained.

10. A method for determining a target sequence of a nucleic acid polymer comprising the steps of:

(a) forming, through a plurality of chemical reactions, a set of products from said nucleic acid polymer wherein
 (i) members of said set of products are selected according to a code;
 (ii) said code specifies a set of weights with which to set the proportions of each of different members of said set of products; and
 (iii) at least one of said set of weights has a value substantially different than that of the other members of said set of weights;

(b) obtaining a set of signals from said set of products; and (c) applying means using said code and said set of signals to recover a sequence of bases;

wherein the target sequence of nucleic acid is determined with accuracy.

11. The invention defined in claim 10 wherein said means using said code and said set of signals to recover said sequence of bases is soft decoding implemented by:

(a) forming a measure of distance between the said signals and a plurality of sets of test signals where each set of test signals is formed based on different hypothesized sequences; and (b) choosing as the determined target sequence the hypothesized sequence whose test signals had the shortest distance to said signals;

whereby an accurate sequence is obtained.

12. The invention as defined in claim 11 wherein said set of products are formed from fragments whose starting sequences are offset from the start sequence of said nucleic acid molecule via using primers to achieve different offsets.

13. The invention as defined in claim 10 wherein said set of products are formed from fragments whose starting sequences are offset from the start sequence of said nucleic acid molecule via using primers to achieve different offsets.

14. A method for determining a target sequence of a single-stranded DNA molecule comprising the steps of:

(a) forming through a plurality of chemical reactions, a set of products from said single-stranded DNA molecule wherein:
 (i) members of said set of products are selected according to a code;
 (ii) said code specifies a set of offsets;
 (iii) each member of said set of products corresponds to a copy of said single-stranded DNA that has been shifted by a number of bases as given by the corresponding member of said set of offsets;

(b) obtaining a set of signals from said set of products where each signal is a summation of the contributions from each member of said set of products wherein each base in the original target will contribute substantially to peaks in the signal at a set of positions corresponding to the sum of a said set of offsets and said base's position in the target; and (c) applying means using said code and said set of signals to recover a sequence of bases;

wherein the target sequence of nucleic acid is determined with accuracy.

15. The invention defined in claim 14 wherein said means using said code and said set of signals to recover said sequence of bases is hard decoding implemented by:

(a) forming from said set of signals a set of quantized signals with the value of each sample of each of said quantized signals being directly translatable to the number of offsets contributing significantly to the peak at that location;

(b) forming a measure of distance between said quantized signals and each set of a plurality of sets of test signals where each set of test signals is formed based on a different hypothesized sequence; and (c) choosing as the determined target sequence the hypothesized sequence whose test signals had the shortest distance to said quantized signals whereby an accurate sequence is obtained.

16. The invention defined in claim 14 wherein said means using said code and said set of signals to recover said sequence of bases is soft decoding implemented by:

(a) forming a measure of distance between the said signals and each set of a plurality of sets of test signals where each set of test signals is formed based on different hypothesized sequences; and (b) choosing as the determined target sequence a hypothesized sequence whose test signals had the shortest distance to said signals;

whereby an accurate sequence is obtained.

17. The invention as defined in claim 14 wherein said set of products are formed from fragments whose starting sequences are offset from the start sequence of said single-stranded DNA molecule via using primers to achieve different offsets.

18. The invention defined in claim 17 wherein said means using said code and said set of signals to recover said sequence of bases is hard decoding implemented by:

(a) forming from said set of signals a set of quantized signals with the value of each sample of each of said quantized signals being directly translatable to the number of offsets contributing significantly to the peak at that location;

(b) forming a measure of distance between said quantized signals and each set of a plurality of sets of test signals where each set of test signals is formed based on a different hypothesized sequence; and (c) choosing as the determined target sequence the hypothesized sequence whose set of test signals had the shortest distance to said quantized signals;

whereby an accurate sequence is obtained.

19. The invention defined in claim 17 wherein said means using said code and said set of signals to recover said sequence of bases is soft decoding implemented by:

(a) forming a measure of distance between the said signals and each set of a plurality of sets of test signals where each set of test signals is formed based on a different hypothesized sequence; and (b) choosing as the determined target sequence the hypothesized sequence whose test signals had the shortest distance to said signals;

whereby an accurate sequence is obtained.

* * * * *

SEQUENCE LISTING

<160> NUMBER OF SEQ ID NOS: 2

<210> SEQ ID NO 1
<211> LENGTH: 15
<212> TYPE: DNA

-continued

```
<213> ORGANISM: Artificial Sequence
<220> FEATURE:
<223> OTHER INFORMATION: arbitrary random sequence chosen to illustrate
      concept

<400> SEQUENCE: 1
caagtaccga gctga                                                    15

<210> SEQ ID NO 2
<211> LENGTH: 10
<212> TYPE: DNA
<213> ORGANISM: Artificial Sequence
<220> FEATURE:
<223> OTHER INFORMATION: last ten bases of sequence 1

<400> SEQUENCE: 2
accgagctga                                                          10
```